United States Patent
Ludwig (10) Patent No.: US 7,382,459 B2
(45) Date of Patent: Jun. 3, 2008

(54) SPECTROSCOPIC GAS SENSOR, IN PARTICULAR FOR DETECTING AT LEAST ONE GAS COMPONENT IN THE AMBIENT AIR, AND METHOD FOR MANUFACTURING A SPECTROSCOPIC GAS SENSOR OF THIS TYPE

(75) Inventor: Ronny Ludwig, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 441 days.

(21) Appl. No.: 11/144,183

(22) Filed: Jun. 2, 2005

(65) Prior Publication Data
US 2005/0270536 A1    Dec. 8, 2005

(30) Foreign Application Priority Data
Jun. 4, 2004    (DE)    ............. 10 2004 027 512

(51) Int. Cl.
*G01N 21/00*    (2006.01)
(52) U.S. Cl. .............. 356/437; 356/439; 356/440; 250/343
(58) Field of Classification Search ........ 356/437–440, 356/432; 250/343, 349, 345, 344, 353; 438/64, 438/51, 106; 29/595
See application file for complete search history.

(56) References Cited

U.S. PATENT DOCUMENTS

| | | | |
|---|---|---|---|
| 4,808,812 A * | 2/1989 | Tanaka et al. ............. 250/216 | |
| 5,801,374 A | 9/1998 | Campbell et al. | |
| 5,897,338 A * | 4/1999 | Kaldenberg ............... 438/116 | |
| 6,016,203 A * | 1/2000 | Martin .................... 356/432 | |
| 6,303,013 B1 * | 10/2001 | Watanabe et al. .......... 204/428 | |
| 6,395,585 B2 * | 5/2002 | Brandl .................... 438/127 | |
| 6,538,251 B1 * | 3/2003 | Weckström et al. ........ 250/343 | |
| 6,618,927 B2 * | 9/2003 | Tajima et al. ............... 29/595 | |
| 6,710,348 B1 | 3/2004 | Rothley et al. | |
| 6,753,967 B2 * | 6/2004 | Stuttard .................. 356/437 | |
| 6,989,549 B2 * | 1/2006 | Diekmann et al. ......... 250/573 | |
| 7,034,304 B2 * | 4/2006 | Tice et al. ................ 250/343 | |
| 7,268,351 B2 * | 9/2007 | Ludwig ................ 250/339.13 | |
| 7,268,882 B2 * | 9/2007 | Fischer et al. ............. 356/437 | |

FOREIGN PATENT DOCUMENTS

| | | |
|---|---|---|
| DE | 10318501 | 1/2005 |
| GB | 2192709 | 1/1998 |
| JP | 7120314 | 5/1995 |
| JP | 7190852 | 7/1995 |
| JP | 7260578 | 10/1995 |
| JP | 11271221 | 10/1999 |
| WO | WO02059551 | 8/2002 |

* cited by examiner

Primary Examiner—L. G. Lauchman
(74) Attorney, Agent, or Firm—Kenyon & Kenyon LLP (57) ABSTRACT

A spectroscopic gas sensor is provided, in particular to detect at least one gas component in the ambient air, and a method for the manufacture of a spectroscopic gas sensor of this type. The gas sensor includes the following: at least one radiation detection device for detecting a radiation spectrum that is characteristic for the at least one gas component; a package for receiving the at least one radiation detection device, having at least one package wall end section; and at least one optical component having at least one connecting section that is connectable to the at least one package wall end section by hot-caulking the at least one package wall end section.

17 Claims, 6 Drawing Sheets

SPECTROSCOPIC GAS SENSOR, IN PARTICULAR FOR DETECTING AT LEAST ONE GAS COMPONENT IN THE AMBIENT AIR, AND METHOD FOR MANUFACTURING A SPECTROSCOPIC GAS SENSOR OF THIS TYPE

FIELD OF THE INVENTION

The present invention relates to a spectroscopic gas sensor, in particular for detecting at least one gas component in the ambient air, and a method for manufacturing a spectroscopic gas sensor of this type.

BACKGROUND INFORMATION

Although applicable to any gas component, the present invention and its underlying object are explained in greater detail below in relation to the concentration of carbon dioxide in the ambient air.

The detection of carbon dioxide is necessary in many different areas. For example, indoor air in rooms is monitored to determine the ambient air quality or to control ventilation and air-conditioning systems, for example in automotive applications. A limiting value for carbon dioxide, is, for example, 1,000 ppm. Carbon dioxide also occurs in gaseous form in food storage facilities and greenhouses, where it is added to the air, and its concentration must be monitored.

Carbon dioxide sensors are used in general to control concentrations in these applications, and sensors are also desirable in portable warning equipment, the people carrying the warning equipment working in the corresponding areas of application. Warning equipment of this type could also be used in areas where people come into contact with elevated concentrations of $CO_2$, for example of approximately 1%. Applications include, for example, silos and wine cellars, where life-threatening situations can occur if carbon dioxide is not monitored.

Up to now, carbon dioxide sensors have been represented, for example, by electrochemical cells. In this case, the reaction between Nasicon ($NaO_2$) and $CO_2$ should be mentioned. Optical systems based on selective adsorption in the near infrared range by a band in the carbon dioxide spectrum are also used for detection purposes.

In principle, spectroscopic gas sensors of this type include a premolded package, forming a chip package which is manufactured in a molding process by extrusion-coating a specially designed metal carrier strip, known as a lead frame, with plastic or an epoxy resin-based molding compound. According to the related art, the premolded package or lead frames are generally formed in such a way that the connectors needed for electrical connection are provided on at least two side edges or on all four side edges of the package. As a result, the premolded package must be mounted flat on the p.c. board, for example via an adhesive or soldered connection. Once the actual sensor chips have been mounted in the package and are suitably contacted, depending on the application, the package is ordinarily closed by a metal cover having apertures for incident radiation and to prevent stray radiation. The metal cover is usually permanently connected to the edge of the package.

Particularly for optical applications in premolded packages, i.e., for optical chips in a premolded package which is mounted flat on a p.c. board, in which the optical axis of the sensor system is positioned, for example, at a 90° angle relative to the p.c. board, the optical radiation must be deflected over or onto the p.c. board by an additional reflector. Conventionally, an additional reflector of this type is mounted on the p.c. board, and in some circumstances over the premolded package, in an additional assembly step.

However, this conventional approach has proven to have a disadvantage in that it is difficult to orient the reflecting surfaces when mounting the additional reflector on the p.c. board using an adhesive and/or soldering process. Imprecise deflection angles frequently occur, preventing optimum detection of the radiation by the optical chip on the p.c. board.

Furthermore, separate consecutive method steps are required for mounting the metal cover and the additional reflector, which results in a complicated process sequence and an expensive method.

SUMMARY

An object of the present invention is to provide a spectroscopic gas sensor that can be manufactured in a simpler and more economical manner, and which ensures better integration of optical components into the sensor package.

According to an example embodiment of the present invention, the spectroscopic gas sensor has at least one radiation detection device for detecting a radiation band that is characteristic for the gas component to be detected; a package for accommodating the at least one detecting unit, which includes at least one package wall end section; and at least one optical component that has a connecting section that is connectable to the at least one package wall end section by hot caulking.

The example spectroscopic gas sensor may have the advantages over conventional approaches in that the spectroscopic gas sensor may be mounted on an assigned p.c. board having, for example, an optical axis parallel to the p.c. board without using additional reflectors. Specifically, a single component performs the functions of both a reflector and a mounted cover, this multifunctional component being mountable in a simple and economical manner together with the sensor package via a combined method step. In comparison to mounting on the p.c. board by soldering, the optical components may be very precisely mounted on and oriented with the premolded package with regard to the optical chips in the package. This ensures optimum deflection of the incident radiation.

In addition, the dimensions of a reflector connected directly to the package may be smaller than the dimensions of a reflector designed for mounting on the p.c. board. This means, for example, that the overall size of the spectroscopic gas sensor system may be very small. Furthermore, this provides a sensor package that is suitable for automotive applications, it being also possible to passivate all stress-sensitive surfaces and contacts in the package.

According to a preferred embodiment, the package is designed as a premolded package using an injection-molding method. This enables a lead frame to be easily extrusion-coated with a package.

According to a further preferred embodiment, an optical component is designed as a reflector for deflecting and/or concentrating the radiation. The reflector is preferably made of a coated plastic and has, for example, at least one parabolic, elliptic or otherwise shaped reflecting surface. A suitable design of the reflecting surfaces of the reflectors makes it possible to additionally concentrate and focus the radiation for deflection purposes.

According to a further preferred embodiment, an optical component is designed as an optical screen that is made, for example, of steel and has an aperture above the chip system. This makes it possible to easily filter out unwanted stray radiation.

Both the reflector and the screen are preferably bondable to the package wall end section by a combined hot caulking process, using a form punch. This provides a simple, economical and reliable bonding step. The bonding sections of both the reflector and the screen are each in a more or less form-fitting contact with a circumferential contact section of the package. This ensures precise orientation of the reflecting surfaces and optimum radiation deflection.

According to a further preferred embodiment, the package wall end section surrounds the associated connecting sections of the optical components and has a deformation section that extends beyond the respective connecting sections. This makes it possible to bend the deformation section of the package in the direction of the associated connecting sections by exerting a predetermined force via the form punch during the hot caulking process to clamp the connecting sections of the optical components in place.

The optical components and the premolded package preferably have a degree of parallelism that enables the package to be mounted on a p.c. board using a standard assembly and vacuum tools. Pick-and-place assembly methods of this type are a simple and economic assembly variant.

The spectroscopic gas sensor is designed, for example, as a two-channel carbon-dioxide/nitrogen oxide gas sensor or a similar device. According to this design, two adjacent sensor units are preferably provided in a single unit, one sensor serving as the reference sensor. Each sensor unit preferably has a thermopile chip that is hermetically sealed by a silicon cap, is mounted on the package and is contacted with suitable package terminals by bond wires. An optical filter chip is attached to each thermopile chip, one of the filter chips having the central wavelength for the at least one gas component to be detected and the other filter chip having a reference spectrum.

BRIEF DESCRIPTION OF THE DRAWINGS

Exemplary embodiments of the present invention are explained in greater detail below with reference to the figures. The figures illustrate particularly advantageous exemplary embodiments of the present invention in greater detail.

DETAILED DESCRIPTION OF EXAMPLE EMBODIMENTS

In the figures, identical reference numbers identify the same or functionally equivalent components.

Figure 1:
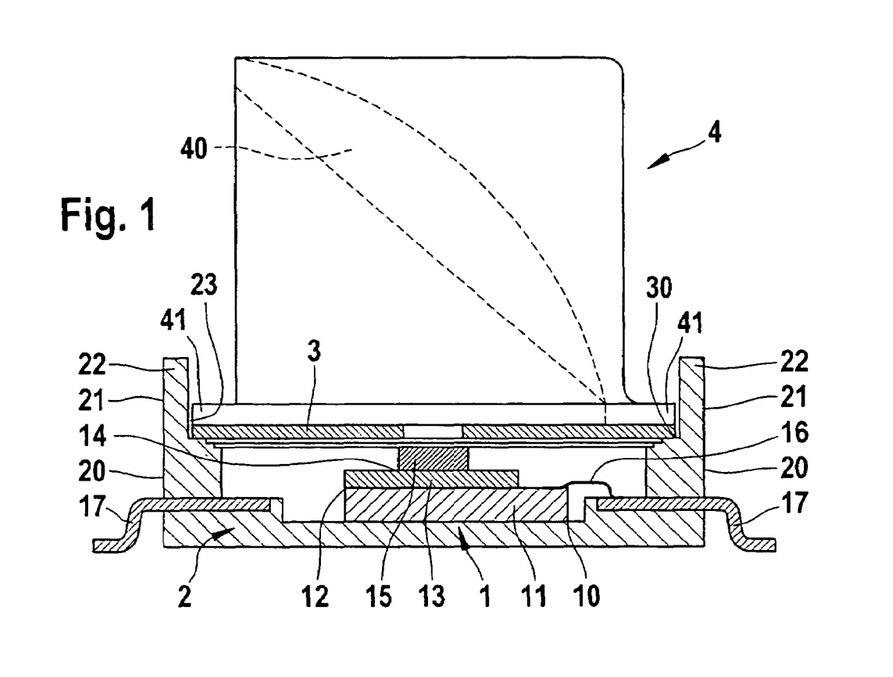
FIG. 1 shows a cross-sectional side view of a spectroscopic gas sensor prior to a hot caulking process according to an exemplary embodiment of the present invention.

FIG. 1 illustrates a cross-sectional side view of a spectroscopic gas sensor prior to the hot caulking process according to an exemplary embodiment of the present invention.

As shown in FIG. 1, the spectroscopic gas sensor preferably includes a radiation detection device 1, which is used to detect a spectrum of an incident radiation that is characteristic for the gas component to be detected. The radiation may be detected in this manner, for example, using an absorber material that heats up as a result of the incident radiation and thus undergoes an increase in temperature that is measurable, for example as thermoelectric voltage. The radiation to be measured, which penetrates the gas surrounding the spectroscopic gas sensor, is absorbed by the molecules contained in the gas within a predetermined frequency range so that, on the basis of the spectrum detected by the radiation detection device, conclusions may be drawn about the concentration of the gas to be detected. Two-channel gas sensors that include an optical chip for detecting the incident radiation and an adjacent chip as a reference chip are generally conventional. Gas sensors of this type are sufficiently well known so that it is unnecessary to describe their operation in detail.

As further shown in FIG. 1, radiation system 1 includes, for example, two adjacent detection units, as mentioned above, each of which has a thermopile chip 11, 11', which, for example, is permanently bonded to the bottom of an extrusion-coated package 2 by a chip adhesive 10, 10'; and a cap provided thereon which is transparent to IR radiation, for example a silicon cap 13, 13' that is advantageously mounted on thermopile chips 11 and 11', respectively, by a seal glass bond 12, 12'. Optical filter chips 15 and 15' which filter out the spectrum or frequency band that is characteristic for the gas to be detected, or filters out the desired reference spectrum for the reference unit, are mounted on silicon caps 13, 13', for example using an optically transparent adhesive 14, 14'.

As is further illustrated in FIG. 1, the units of radiation detection device 1 are connected via bond wires 16 to suitable connecting areas 17 for measuring the thermoelectric voltage which occurs. Bond wires 16 and the surrounding chip area are cast, for example, in silicone gel so that the filter chip surfaces advantageously remain free of gel.

Package 2 preferably has the structure illustrated in FIG. 1 and is manufactured in a molding process by extrusion-coating a specially designed metal carrier strip, known as a lead frame, with plastic or a molding compound which is based, for example, on epoxy resin. The package is, for example, rectangular or round in shape and has a bottom area that accommodates radiation detection device 1 and preferably also has a circumferential package wall 20. As illustrated in FIG. 1, the inner circumferential surface of package wall 20 preferably includes a circumferential contact surface 23 that is designed, for example, as step 23 so that additional structural components, preferably optical components 3, 4, may be inserted from above in a form-fitting manner into the package and onto circumferential contact surface 23. Circumferential contact surface 23 may also be designed in a different manner, for example as merely partially provided stepped areas, as insertion notches or similar elements.

Package wall 20 also includes a package wall end section 21 having a preferably circumferential deformation section 22. The specific design and function of deformation section 22 is explained in greater detail below.

The spectroscopic gas sensor further includes an optical screen 3 having an aperture that protects against stray radiation. Screen 3 has a connecting section 30 that is designed, according to the present exemplary embodiment, as a circumferential edge section of optical screen 3. The dimensions of package 2 and optical screen 3 are matched to each other so that the connecting section 30 of screen 3 may be inserted in a more or less form-fitting manner onto circumferential contact surface 23 of the inner circumferential surface of package 2. Contact surface 23 of package 2 and connecting section 30 of optical screen 3 are advantageously designed so that, when mounted, the plane defined by the optical screen is positioned parallel with the plane of optical chips 15 and 15'. This enables the package to be mounted on p.c. boards using standard assembly methods and vacuum tools. A pick-and-place process of this type is a simple and economical assembly method.

As is further illustrated in FIG. 1, the spectroscopic gas sensor also has a reflector 4 that is used to reflect or deflect to optical filter chips 15 and 15' the radiation illuminating the gas to be detected and also to preferably concentrate this radiation. Like optical screen 3, reflector 4 includes a connecting section 41, preferably a circumferential connecting edge 41, which, in turn, is dimensioned so that it may be placed onto circumferential contact surface 23 of package 2 or, if an optical screen 3 is provided, onto optical screen 3 in a way that positions it in a more or less form-fitting manner. Contact surface 23 of package 2 and connecting section 41 of reflector 4 are matched in a way that establishes a degree of parallelism between the premolded package, i.e., optical filter chips 15 and 15' and the reflector surfaces when reflector 4 is inserted into package 2. This makes it possible to use an assembly method based on the advantageous pick-and-place process mentioned above. In addition, mounting reflector 4 in package 2 in this parallel and form-fitting manner ensures that the incident radiation is precisely deflected onto the absorber surface or optical filter chips 15 and 15'.

Figure 2:
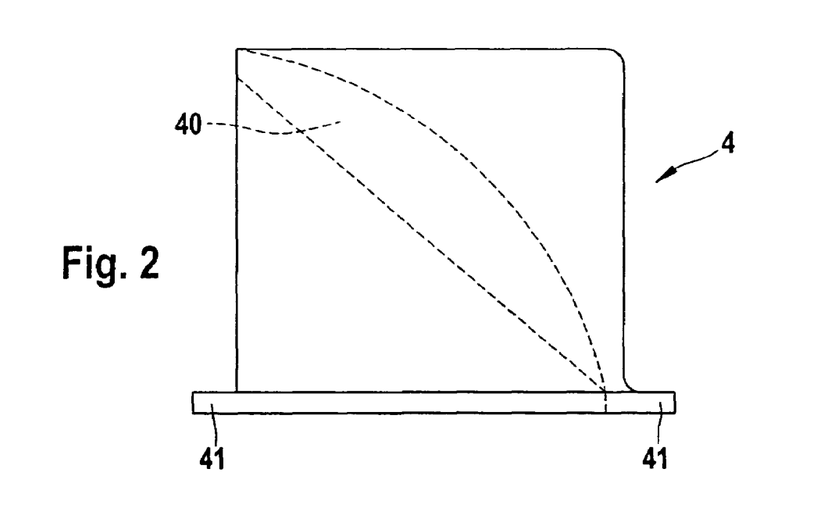
FIG. 2 shows a side view of a reflector according to an exemplary embodiment of the present invention.
Figure 3:
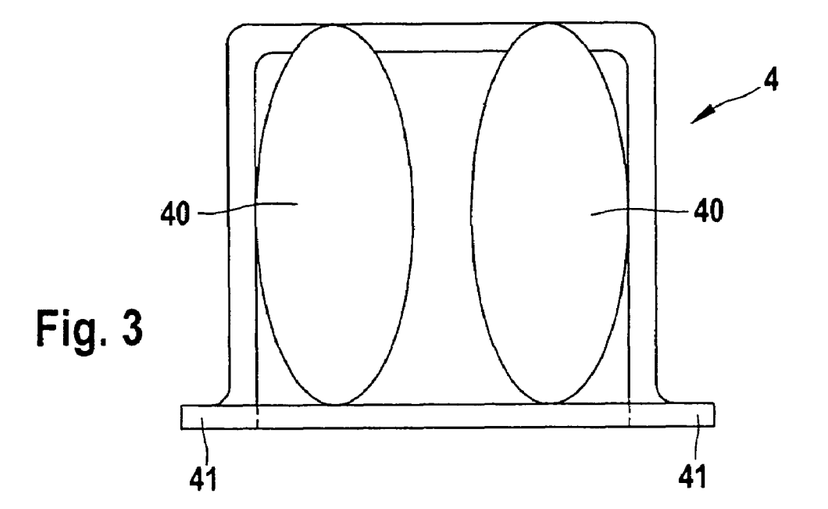
FIG. 3 shows a front view of a reflector according to the exemplary embodiment in FIG. 2.
Figure 4:
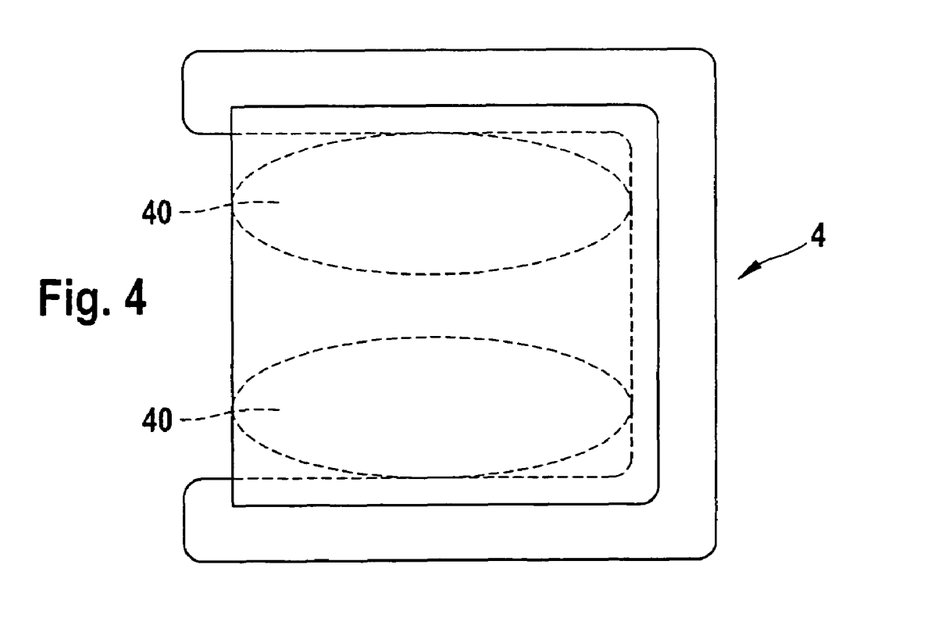
FIG. 4 shows a top view of a reflector according to the exemplary embodiment in FIGS. 2 and 3.

FIGS. 2, 3, and 4 illustrate a side view, a front view and a top view of a reflector 4 according to a preferred exemplary embodiment of the present invention. As illustrated in FIGS. 2, 3 and 4, reflector 4 preferably includes two reflecting surfaces 40, each of which is assigned to one of the two units of radiation detection device 1. Reflector 4 is injection-molded, for example in plastic, and coated with a metallic layer having a high reflection coefficient; reflecting surfaces 40 may have a parabolic, elliptical or otherwise shaped design according to the application at hand. The only determining factor is that the incident radiation be deflected and concentrated in an optimum manner onto the associated optical filter chips 15, 15'.

A reflector 4 according to the present exemplary embodiment may be used, for example, to deflect by a 90-degree angle in the direction of optical filter chips 15 and 15' and concentrate radiation parallel to the p.c. board surface or the bottom surface of package 2. It is obvious to those skilled in the art that by suitably inclining reflecting surfaces 40 of reflector 4, it is possible to set other deflection angles and thus optimally deflect or reflect radiation that is incident at a different angle. As mentioned above, reflector 4 may, for example, be made of injection-molded plastic that is coated with a reflective material.

Figure 5:
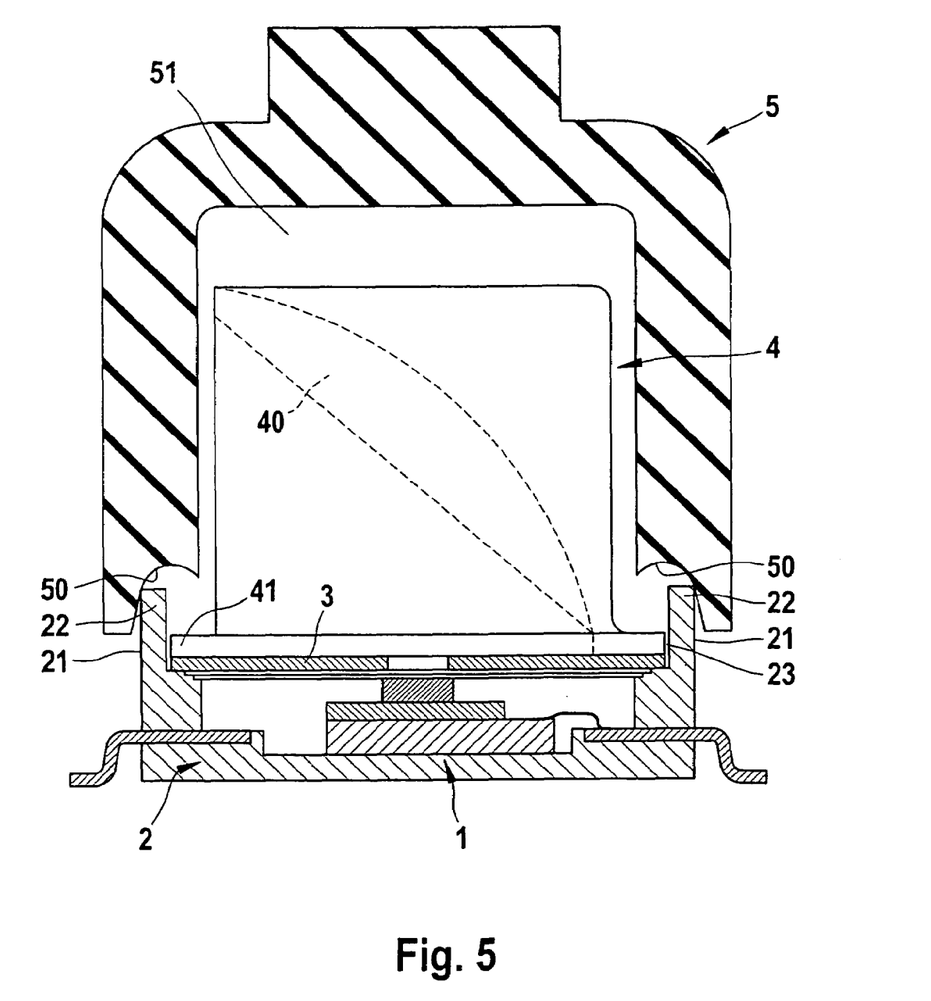
FIG. 5 shows a cross-sectional side view of a spectroscopic gas sensor during the hot caulking process according to an exemplary embodiment of the present invention.

FIG. 5 shows a cross-sectional side view of the spectroscopic gas sensor according to FIG. 1 at the beginning of the hot caulking process.

As mentioned above, package 2 has a package wall end section 21, which has a preferably circumferential deformation section 22. A predetermined length of deformation section 22 extends beyond connecting sections 30 of optical screen 3 or beyond connecting sections 41 of reflector 4 after the latter has been inserted. The projecting length of deformation section 22 is more or less equal to the exposed area of connecting sections 30 and 41, so that if deformation section 22 is bent in the direction of connecting sections 30 and 41, it does not disadvantageously come into contact with the package of reflector 4.

A form punch 5 that has a receptacle area 51 for receiving reflector 4 is used for the hot caulking process. Receptacle area 51 is dimensioned so that, when form punch 5 is placed over the spectroscopic gas sensor, the inner surface of form punch 5 does not come into contact with the outer surface of reflector 4, which prevents damage to reflector 4 during the hot caulking process. In addition, as illustrated in FIG. 5, form punch 5 has a deformation contact surface 50 that comes to rest against deformation section 22 of package 2 when form punch 5 is placed over the spectroscopic sensor. According to the present exemplary embodiment, deformation contact surface 50 is dimensioned and designed, for example, with a concave curvature so that when force is applied vertically to form punch 5 in the direction of the p.c. board or bottom surface of package 2, deformation section or deformation sections 22 are bendable along the concave curvature surface of deformation contact surface 50 in the direction of connecting section 41. Form punch 5 is made, for example, of steel or another heat-conducting material and is heated to a temperature of, for example, approximately 240 degrees Celsius, at which deformation section 22 softens for deforming deformation section 22 when form punch 5 comes into contact with deformation section 22. The temperature must be selected so that deformation section 22 of package 2 merely softens but does not melt or bond when it comes into contact with heated deformation contact surface 50 of form punch 5.

Figure 6:
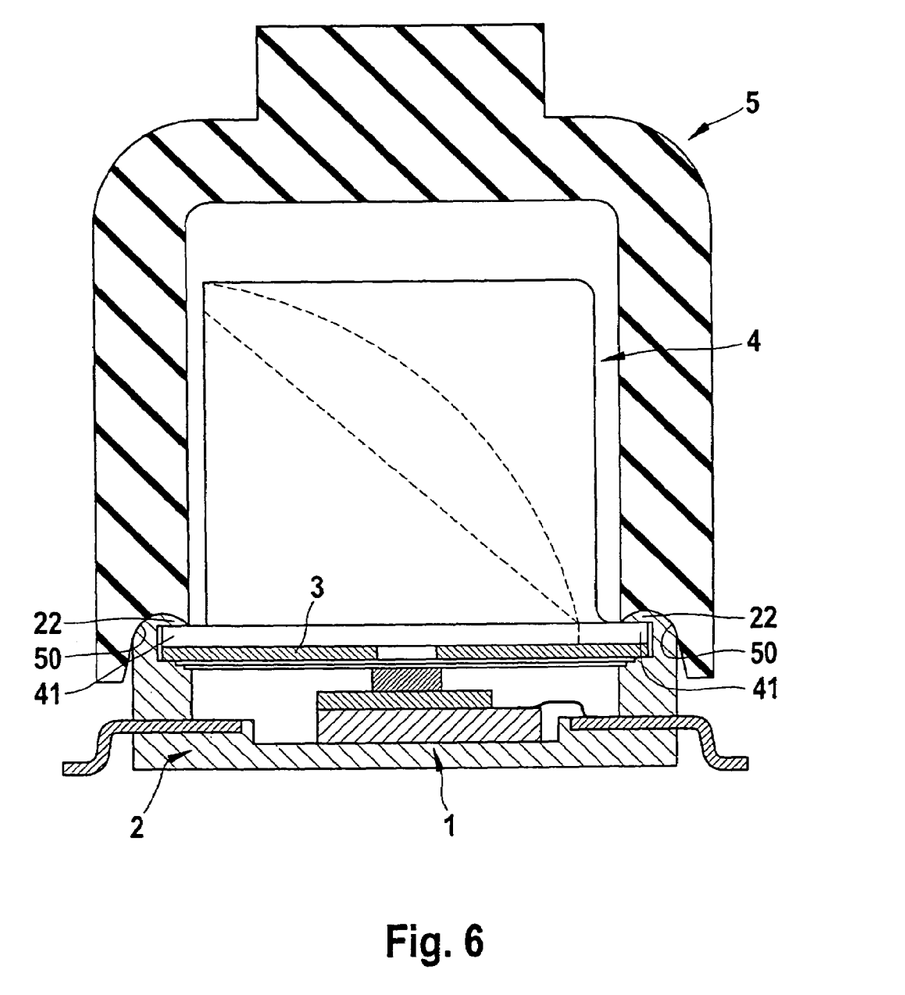
FIG. 6 shows a cross-sectional side view of a spectroscopic gas sensor during the hot caulking process according to an exemplary embodiment of the present invention.

FIG. 6 illustrates a cross-sectional side view of the spectroscopic gas sensor according to FIGS. 1 and 5 during and at the end of the hot caulking process. FIG. 6 shows that the one or more deformation sections 22 of package 2 are bent and deformed via form punch 5 in the direction of connecting sections 30 and 41 so that optical screen 3 and reflector 4 are clamped between contact surface 23 of package 2 and the one or more deformation sections 22 of package 2. As is further illustrated in FIG. 6, the deformation of deformation section 22 follows the predetermined curvature of deformation contact surface 50 of form punch 5.

Figure 7:
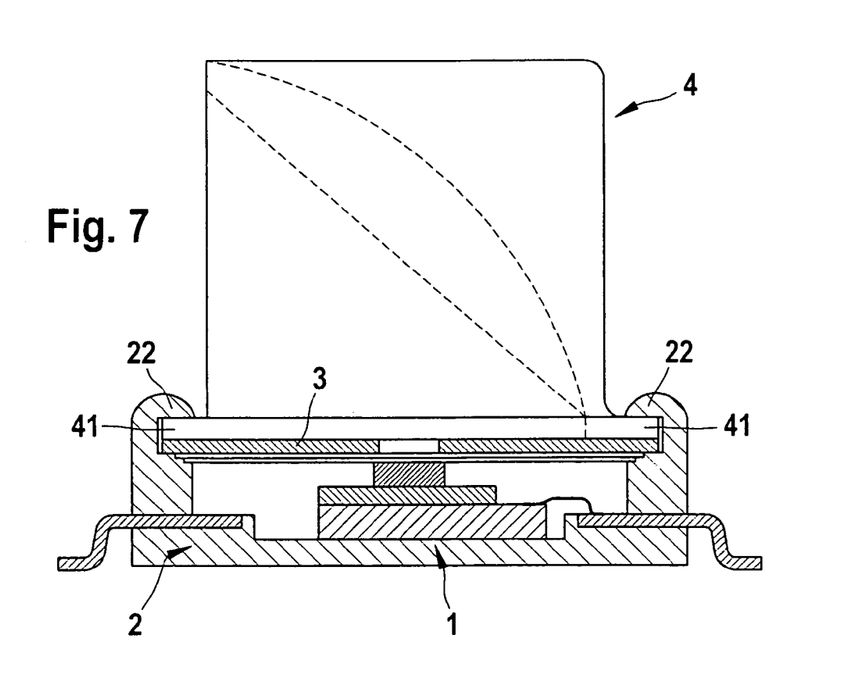
FIG. 7 shows a cross-sectional side view of a spectroscopic gas sensor after the hot caulking process according to an exemplary embodiment of the present invention.
Figure 8:
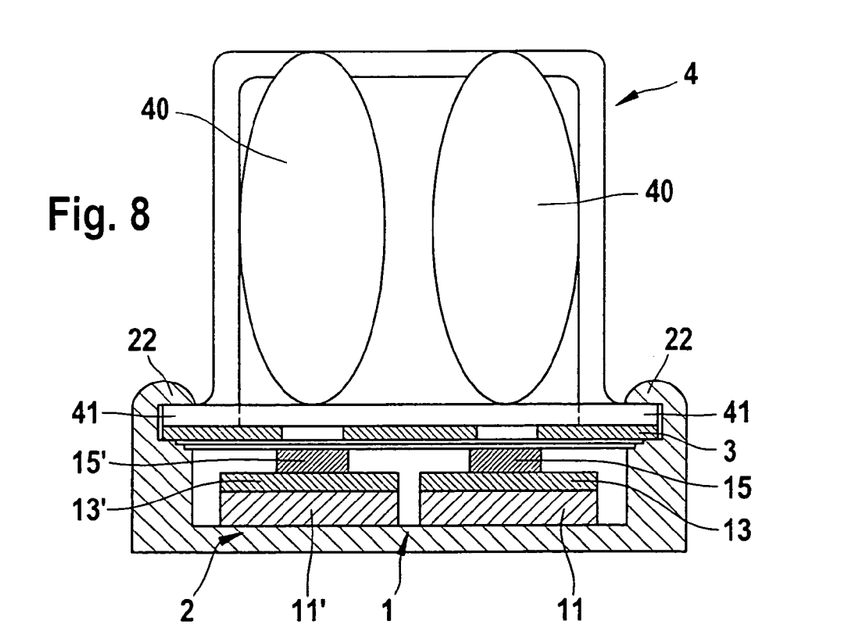
FIG. 8 shows a cross-sectional view of the spectroscopic gas sensor from FIG. 7, viewed from the front.

Bent deformation sections 22 are subsequently cooled to obtain the finished spectroscopic gas sensor illustrated in FIG. 7. FIG. 7 shows a cross-sectional side view and FIG. 8 a cross-sectional front view of the finished spectroscopic gas sensor according to the present exemplary embodiment.

Figure 9:
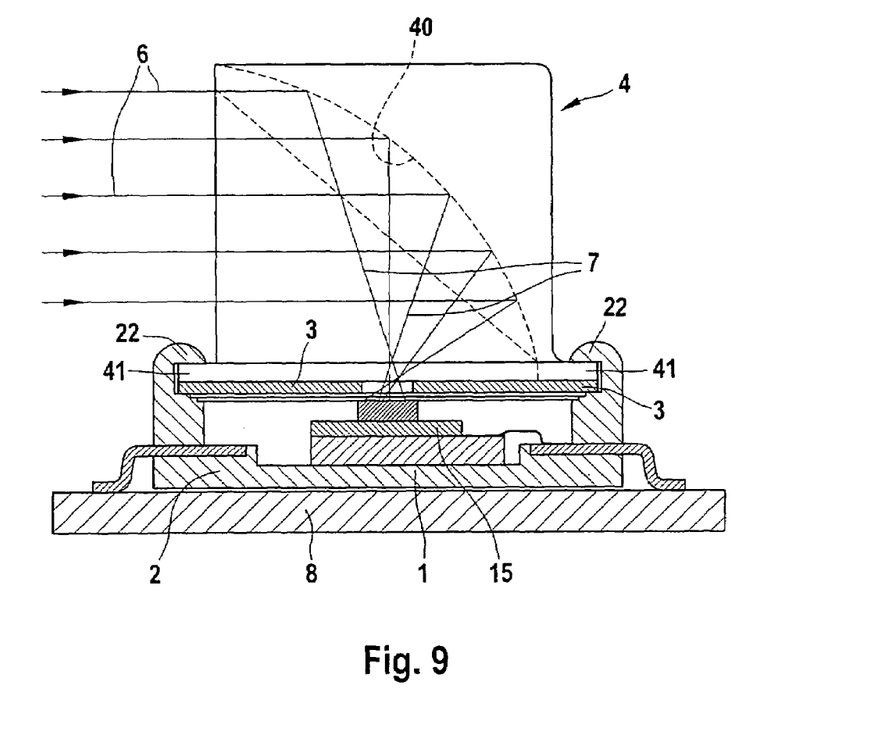
FIG. 9 shows a cross-sectional side view of a spectroscopic gas sensor having incident and reflected radiation according to an exemplary embodiment of the present invention.

FIG. 9 shows the operation of the completed spectroscopic gas sensor in a schematic cross-sectional side view. It is apparent that an incident radiation 6 oriented parallel to p.c. board 8 is reflected by reflector 4 by a 90-degree angle in the direction of the opening of optical screen 3 and in the direction of radiation detection device 1. In FIG. 9, this is identified by reflected beam path 7. As further illustrated in FIG. 9, the completed spectroscopic gas sensor is subsequently mounted on an assigned p.c. board 8 or a substrate 8.

The present invention thus provides a spectroscopic gas sensor and a method for the manufacture thereof, which easily ensures a precisely positioned and oriented clamping of optical components, for example an optical screen and/or a reflector, in the gas sensor package. In addition, reflector 4 is simultaneously used as a protective cover, making it unnecessary to provide an additional metal cover.

Although the present invention was described above on the basis of preferred exemplary embodiments, it is not limited thereto but may be modified in a plurality of ways.

For example, the optical components may be inserted into the package and oriented using an adhesive or similar connection instead of via contact with the circumferential contact surface of the package.

LIST OF REFERENCE NUMERALS

| | |
|---|---|
| 1 | Radiation detection device |
| 2 | Package |
| 3 | Optical screen |
| 4 | Reflector |
| 5 | Form punch |
| 6 | Incident radiation |
| 7 | Reflected radiation |
| 8 | P.C. board |
| 10, 10' | Chip adhesive |
| 11, 11' | Thermopile chip |
| 12, 12' | Seal glass bond |
| 13, 13' | Silicon cap |
| 14, 14' | Optical adhesive |
| 15, 15' | Optical filter chip |
| 16 | Bond wire |
| 17 | Connecting area |
| 20 | Package wall |
| 21 | Package wall end section |
| 22 | Deformation section |
| 23 | Circumferential contact surface |
| 30 | Connecting section |
| 40 | Reflecting surface |
| 41 | Connecting section |
| 50 | Deformation contact surface |
| 51 | Receptacle area |

What is claimed is:

1. A spectroscopic gas sensor for detecting at least one gas component in ambient air, comprising:
   at least one radiation detection device configured to detect a radiation spectrum that is characteristic for the at least one gas component;
   a package for receiving the at least one radiation detection device, the package having at least one package wall end section; and
   at least one optical component having at least one connecting section that is connectable to the at least one package wall end section by hot caulking the at least one package wall end section,
   wherein the at least one optical component includes a reflector and a screen, wherein both the reflector and the screen are connectable to the at least one package wall end section using a joint hot caulking process with the aid of a form punch.

2. The gas sensor as recited in claim 1, wherein the package is configured as a premolded package using an injection-molding process.

3. The gas sensor as recited in claim 1, wherein the reflector is used for at least one of deflecting and concentrating, the radiation.

4. The gas sensor as recited in claim 3, wherein the reflector is made of a plastic coated with a reflective material.

5. The gas sensor as recited in claim 3, wherein the reflector has at least one reflecting surface.

6. The gas sensor as recited in claim 5, wherein a shape of the reflecting surface is one of parabolic or elliptical.

7. The gas sensor as recited in claim 1, wherein the screen is an optical screen.

8. The gas sensor as recited in claim 7, wherein the optical screen is made of steel.

9. The gas sensor as recited in claim 1, wherein the gas sensor is mounted on an assigned p.c. board using a pick-and-place assembly method.

10. The gas sensor as recited in claim 1, wherein the gas sensor is designed as one of a two-channel carbon dioxide gas sensor or nitrogen oxide gas sensor.

11. A spectroscopic gas sensor for detecting at least one gas component in ambient air, comprising:
   at least one radiation detection device configured to detect a radiation spectrum that is characteristic for the at least one gas component;
   a package for receiving the at least one radiation detection device, the package having at least one package wall end section; and
   at least one optical component having at least one connecting section that is connectable to the at least one package wall end section by hot caulking the at least one package wall end section,
   wherein the at least one optical component includes a reflector and a screen, each of the reflector and the screen having a connecting section, wherein the connecting sections of the screen and the reflector are each provided in a form-fitting manner on a circumferential contact section of the package.

12. A spectroscopic gas sensor for detecting at least one gas component in ambient air, comprising:
   at least one radiation detection device configured to detect a radiation spectrum that is characteristic for the at least one gas component;
   a package for receiving the at least one radiation detection device, the package having at least one package wall end section; and
   at least one optical component having at least one connecting section that is connectable to the at least one package wall end section by hot caulking the at least one package wall end section,
   wherein the at least one package wall end section of the package surrounds the connecting section of the at least one optical component and has a deformation section that projects over the connecting section,
   wherein the deformation section is deformable in the direction of the connecting section by a form punch during the hot caulking process to clamp the connecting section of the at least one optical component.

13. A spectroscopic gas sensor for detecting at least one gas component in ambient air, comprising:
   at least one radiation detection device configured to detect a radiation spectrum that is characteristic for the at least one gas component;
   a package for receiving the at least one radiation detection device, the package having at least one package wall end section; and at least one optical component having at least one connecting section that is connectable to the at least one package wall end section by hot caulking the at least one package wall end section, wherein the at least one package wall end section of the package surrounds the connecting section of the at least one optical component and has a deformation section that projects over the connecting section, wherein a predetermined force for bending the deformation section is applicable to the form punch during the hot caulking process without damaging the at least one optical component.

14. A method for manufacturing a spectroscopic gas sensor, the gas sensor for detecting at least one gas component in ambient air, the method comprising:

forming a package for receiving at least one detection device for detecting a radiation spectrum that is characteristic for the at least one gas component, the package having at least one deformation section;

inserting at least one optical component having at least one connecting section into the package so that the at least one deformation section of the package projects over the at least one connecting section; and deforming the at least one deformation section of the package in a direction of the at least one connecting section of the at least one optical component for clamping the at least one optical component in place in the package using a hot caulking process.

15. The method as recited in claim 14, wherein the package is manufactured as a premolded package, using an injection-molding method.

16. The method as recited in claim 14, wherein a form punch having a deformation contact surface is used for the hot caulking process.

17. The method as recited in claim 14, wherein the gas sensor is mounted on an assigned p.c. board, using a pick-and-place assembly method.

* * * * *